US010413025B1

(12) United States Patent
Cwalinski et al.

(10) Patent No.: US 10,413,025 B1
(45) Date of Patent: Sep. 17, 2019

(54) ARRANGEMENT OF CAPSULE BEADS FILLED WITH TOPICAL MATERIAL

(71) Applicants: Saxon Cwalinski, Fort Lauderdale, FL (US); Dustin Cwalinski, Fort Lauderdale, FL (US); Helen Cwalinski, Fort Lauderdale, FL (US)

(72) Inventors: Saxon Cwalinski, Fort Lauderdale, FL (US); Dustin Cwalinski, Fort Lauderdale, FL (US); Helen Cwalinski, Fort Lauderdale, FL (US)

( * ) Notice: Subject to any disclaimer, the term of this patent is extended or adjusted under 35 U.S.C. 154(b) by 0 days.

(21) Appl. No.: 16/110,210

(22) Filed: Aug. 23, 2018

(51) Int. Cl.
*A44C 5/00* (2006.01)
*A44C 15/00* (2006.01)

(52) U.S. Cl.
CPC ............ *A44C 5/003* (2013.01); *A44C 15/005* (2013.01)

(58) Field of Classification Search
CPC ........... F41H 9/10; B05B 7/1413; A44C 5/00; A44C 5/0023; A44C 5/003; A44C 5/02; A44C 15/005; A44C 9/0069; A44C 25/002; A61M 35/00; A61M 35/003; A61M 35/006
USPC ............................ 222/175; 224/148.1, 148.2
See application file for complete search history.

(56) References Cited

U.S. PATENT DOCUMENTS

| | | | | |
|---|---|---|---|---|
| 3,685,284 A * | 8/1972 | Taubner, Jr. | ......... | A44C 11/002 59/2 |
| 4,768,688 A * | 9/1988 | Harrigan | ................ | A44C 5/003 206/37 |
| 4,781,705 A * | 11/1988 | Shepherd | .............. | A61M 35/00 128/897 |
| 4,866,952 A * | 9/1989 | Hight | ................... | A44C 25/002 63/18 |
| 4,951,940 A * | 8/1990 | Vitello | ............... | A63B 21/0602 224/148.1 |
| 5,161,680 A * | 11/1992 | Badgley | ................. | A44C 15/00 206/205 |
| 6,056,729 A * | 5/2000 | Yu | ......................... | A61M 35/00 604/289 |
| 6,126,041 A * | 10/2000 | DiTomasso | ............... | A45F 3/20 222/175 |
| 6,173,866 B1 * | 1/2001 | Taylor, Jr. | ................. | A45F 3/20 222/175 |
| 7,316,332 B2 * | 1/2008 | Powers | .................. | A45D 34/00 222/1 |
| 8,082,753 B1 * | 12/2011 | Alvarez, Jr. | .............. | A45F 3/16 224/148.1 |
| D672,465 S * | 12/2012 | Sherman | ...................... | D24/207 |
| 8,935,940 B1 * | 1/2015 | Lough | ...................... | F41H 9/10 63/1.11 |
| 9,451,797 B1 | 9/2016 | Ashkanani | | |

(Continued)

FOREIGN PATENT DOCUMENTS

GB 2553500 3/2018

*Primary Examiner* — Patrick M. Buechner
(74) *Attorney, Agent, or Firm* — The Concept Law Group, PA; Scott D. Smiley; Scott M. Garrett

(57) ABSTRACT

A wearable hand-sanitizing apparatus includes a series of breakable capsules containing a hand sanitizing gel or fluid. The capsules are linked together and can be worn as a bracelet or a necklace, as desired by the user. Each capsule containing the hand-sanitizing material contains enough material for a single use. The capsules can be ruptured by being squeezed by the user. Some capsules can contain different types of material, such as a moisturizing lotion.

16 Claims, 12 Drawing Sheets

(56) References Cited

U.S. PATENT DOCUMENTS

| | | | |
|---|---|---|---|
| 9,932,133 B2* | 4/2018 | Sherman | A44C 11/002 |
| 2003/0136149 A1* | 7/2003 | Logan | A44C 11/002 |
| | | | 63/35 |
| 2004/0016774 A1* | 1/2004 | Gentzkow | A61J 7/0046 |
| | | | 222/175 |
| 2004/0134229 A1* | 7/2004 | Oliver | A41D 31/0005 |
| | | | 63/37 |
| 2006/0091156 A1* | 5/2006 | Powers | A45D 34/00 |
| | | | 222/175 |
| 2009/0031757 A1* | 2/2009 | Harding | A44C 5/003 |
| | | | 63/3.2 |
| 2009/0089988 A1* | 4/2009 | Johnson, Sr. | A44C 23/00 |
| | | | 27/1 |
| 2011/0127293 A1* | 6/2011 | Pascatore | B65D 83/005 |
| | | | 222/1 |
| 2011/0139823 A1* | 6/2011 | Staudt | A41D 20/00 |
| | | | 222/175 |
| 2011/0155765 A1* | 6/2011 | Properzi | A47K 5/1201 |
| | | | 222/175 |
| 2012/0138637 A1* | 6/2012 | Ciavarella | A44C 5/0023 |
| | | | 224/148.4 |
| 2016/0324227 A1 | 11/2016 | Bowen et al. | |
| 2017/0156454 A1 | 6/2017 | Abadi et al. | |

* cited by examiner

ARRANGEMENT OF CAPSULE BEADS FILLED WITH TOPICAL MATERIAL

FIELD OF THE INVENTION

The present invention relates generally to sanitizing devices, and, more particularly, relates to a wrist-worn bracelet device having a plurality of bead filled with a sanitizing fluid which can be opened by pressure rupture to release the sanitizing fluid.

BACKGROUND OF THE INVENTION

Hand sanitizers have become very popular and can be found in a wide variety of products. In particular, bottled sanitizing gel fluid is sold in a wide variety of containers, from small personal use squeeze bottles to large commercial pump bottles. Carrying a small bottle of hand sanitizer is popular because it is not always convenient to or easy to find a place to wash one's hands, and having a small bottle of hand sanitizer is a much more convenient way to kill microorganisms in many situations. This can be particularly true with young children.

However, carrying a bottle of hand sanitizer is not always convenient. For example, a person's garments lack pockets suitable for carrying a small squeeze bottle. Furthermore, there is a possibility that the bottle may inadvertently get opened, resulting in sanitizing fluid being discharged in the person's pocket. It is also known that dispensing a desired quantity of hand sanitizer from a squeeze bottle can be inconsistent, sometimes dispensing more than desired, and sometimes less, causing the person to dispense more, and possibly dispensing more than desired. Accordingly, to solve these problems, there is a need for a device to carry hand sanitizing fluid in a way that is convenient, does not require pockets, and which can dispense a consistent amount of fluid.

SUMMARY OF THE INVENTION

The invention provides an arrangement of capsule beads filled with topical material that overcomes the hereinaforementioned disadvantages of the heretofore-known devices and methods of this general type and that allows a person to carry several single use portions of topical material with them, without having to carry a bottle or other similar container elsewhere on their person.

With the foregoing and other objects in view, there is provided, in accordance with the invention, a wearable hand sanitizing apparatus for dispensing a sanitizing fluid that includes a plurality of capsule beads, each of which is filled with a quantity of sanitizing fluid and has at least a portion that is configured to rupture upon a pressure being applied to the capsule bead, thereby allowing the sanitizing fluid to be dispensed from the capsule bead. The hand sanitizing apparatus can further include a plurality of linkages coupling the plurality of capsule beads together in a series.

In accordance with another feature, the plurality of capsule beads and linkages are arranged into a circle.

In accordance with another feature, the circle is sized to fit on and be retained on a person's wrist.

In accordance with another feature, the circle is sized to fit around a person's neck.

In accordance with another feature, at least some of the plurality of capsule beads each comprise a compressible hollow body and a rupturable port.

In accordance with another feature, at least some of the plurality of capsule beads each comprise a hollow body having a spherical or ovoid shape.

In accordance with another feature, the plurality of linkages is firmed by a filament that passes through each one of the plurality of capsule beads.

In accordance with another feature, one of the plurality of linkages comprises a clasp.

In accordance with another feature, the plurality of linkages each comprise a pair of oppositely facing coupling members that are configured to couple to an end of a capsule bead which are joined together by a flexible member.

In accordance with another feature, the plurality of linkages are formed of portions of a filament that passes through a portion of each of the plurality of capsule beads, and wherein the filament is coated with a material that is the same as, and contiguous with that of the plurality of capsule beads.

each of the plurality of capsule beads is made of a material including at least one of plastic, gelatin, cellulose, or silicone.

In accordance with some embodiments, there is further provided a bracelet for dispensing a hand sanitizing material that includes a plurality of capsule beads, each of which is filled with a quantity of sanitizing fluid and is configured to rupture upon a pressure being applied to the capsule bead, thereby allowing the sanitizing fluid to be dispensed from the capsule bead. The bracelet further includes at least one connecting member that couples the plurality of capsules together in a series that forms a circle that is sized to fit on and be retained on a person's wrist.

In accordance with another feature, at least some of the plurality of capsule beads each comprise a compressible hollow body and a rupturable port.

In accordance with another feature, at least one connecting member is a filament that passes through each one of the plurality of capsule beads.

In accordance with another feature, the plurality of capsule beads comprises at least one capsule bead filled with a first topical material and at least one capsule bead filled with a second topical material, and wherein the at least one capsule bead filled with the first topical material and the at least one capsule bead filled with the second topical material are visually distinct.

In accordance with another feature, the at least one connecting member is a plurality of linkages which each comprise a pair of oppositely facing coupling members that are each configured to couple to an end of a capsule bead and wherein each pair of oppositely facing coupling members are joined together by a flexible member.

In accordance with another feature, each of the plurality of capsule beads is made of a material including at least one of plastic, gelatin, cellulose, or silicone.

In accordance with another feature, the at least one connecting member is formed exclusively of, and is contiguous with, a material used to form the plurality of capsule beads.

In accordance with some embodiments, there is further provided a bracelet for dispensing a hand sanitizing material that includes a plurality of capsule beads, each of which is filled with a quantity of topical fluid and is configured to rupture upon a pressure being applied to the capsule bead, thereby allowing the topical fluid to be dispensed from the capsule bead. The bracelet can further include a plurality of linkages that each couple two of the plurality of capsule beads together. The bracelet can further include the plurality of capsule beads and linkages being arranged to form a series of capsule beads connected by the linkages.

In accordance with another feature, at least some of the plurality of capsule beads each comprise a hollow body having a spherical or ovoid shape.

Although the invention is illustrated and described herein as embodied in an arrangement of capsule beads containing topical material, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

"In the description of the embodiments of the present invention, unless otherwise specified, azimuth or positional relationships indicated by terms such as "up", "down", "left", "right", "inside", "outside", "front", "back", "head", "tail" and so on, are azimuth or positional relationships based on the drawings, which are only to facilitate description of the embodiments of the present invention and simplify the description, but not to indicate or imply that the devices or components must have a specific azimuth, or be constructed or operated in the specific azimuth, which thus cannot be understood as a limitation to the embodiments of the present invention. Furthermore, terms such as "first", "second", "third" and so on are only used for descriptive purposes, and cannot be construed as indicating or implying relative importance.

In the description of the embodiments of the present invention, it should be noted that, unless otherwise clearly defined and limited, terms such as "installed", "coupled", "connected" should be broadly interpreted, for example, it may be fixedly connected, or may be detachably connected, or integrally connected; it may be mechanically connected, or may be electrically connected; it may be directly connected, or may be indirectly connected via an intermediate medium. As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the length of the member being discussed. Those skilled in the art can understand the specific meanings of the above-mentioned terms in the embodiments of the present invention according to the specific circumstances

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
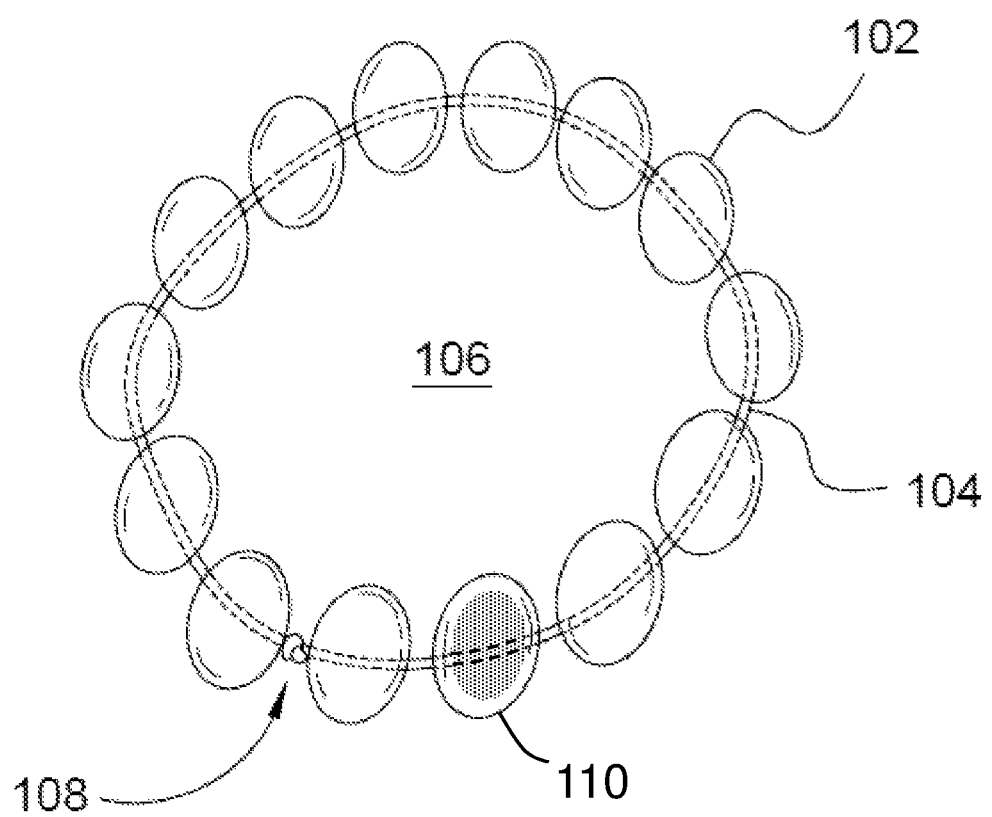
FIG. 1 shows an arrangement of capsule beads filled with a topical material, in accordance with some embodiments.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient hand sanitizing apparatus. Embodiments of the invention provide a convenient and decorative way to carry topical materials like hand sanitizing fluid, without the need to carry one or more bottles or other such containers of the topical material.

FIG. 1 shows an arrangement 100 of capsule beads 102 filled with a topical material, in accordance with some embodiments. As used herein, the term "capsule bead" refers to a hollow structure with walls made of a material that is flexible to allow a person to compress or squeeze the capsule bead, causing it to rupture and thereby release the contents of the capsule bead. The capsule beads 102 contain a topical material in generally a fluid, gel, or paste form such as, for example, sanitizing fluid, moisturizer, sunscreen, and so on. These are materials that a person may wish to dispense and disperse topically, on their skin or on the skin of another person (e.g. a child). The capsule beads 102 are linked or connected together into a series, such as by a filament 104 (e.g. thread, cord) so that the plurality of capsule beads 102 can be arranged into, for example, and circle, with the filament tied in a knot 108, or otherwise joined together such as by a clasp, allowing a person to place a hand through the center 06 of the arrangement 100 to easily carry the plurality of beads. The capsule beads 102 in the arrangement 100 can all be filled with the same topical material, or with different topical materials. When there are multiple topical materials in an arrangement, the capsule beads, such as capsule bead 110, can be made visually distinct (e.g. by size, color, patterns, writing, etc.) to indicate their contents. Each one of the plurality of capsule beads can have, in some embodiments, an internal volume of 0.5 to 2.0 cubic centimeters, and the capsule beads in an arrangement 100 can be of varying sizes.

Figure 2:
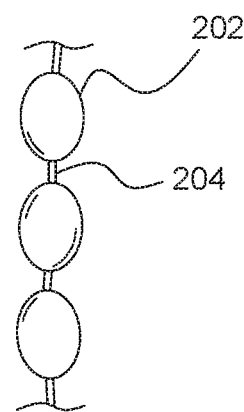
FIG. 2 shows an arrangement of capsule beads, with at least some capsule beads having an ovoid shape, in accordance with some embodiments.

FIG. 2 shows an arrangement 200 of capsule beads 202, with at least some capsule beads having an ovoid shape, in accordance with some embodiments. The arrangement 200 shows a series of connected ovoid capsule beads 202. Other shapes, including spherical, cubical or cuboid, parallelepiped, etc. can also be used. The capsule beads 202 are coupled together with linkages or coupling members 204 between them. For some uses, a particular shape may be preferable over, for example, a spherically shaped capsule bead. For example, an ovoid-shaped capsule bead, being elongated in comparison to a sphere, can have a lower profile/height compared to a spherical capsule bead having the same volume.

Figure 3:
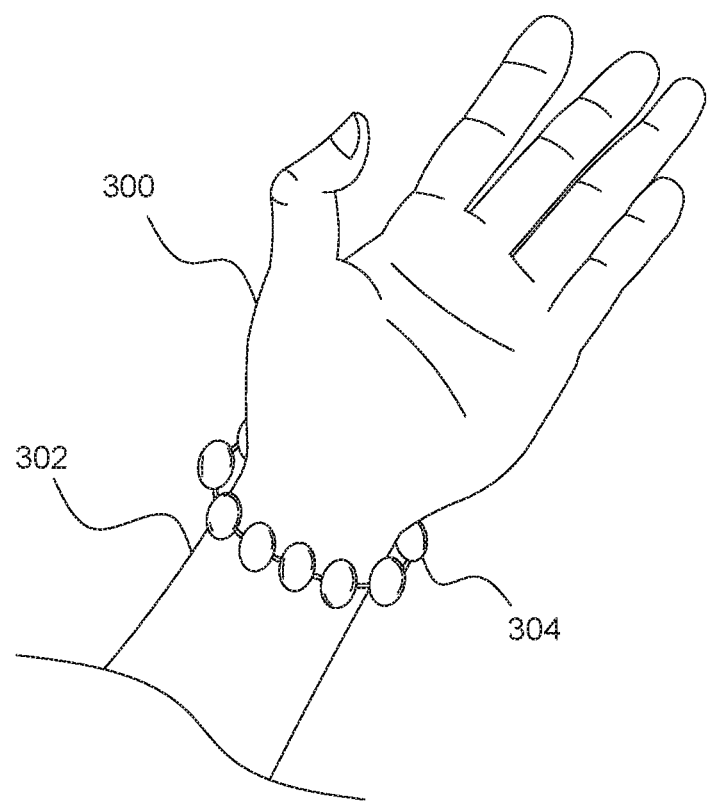
FIG. 3 shows an arrangement of capsule beads in the form of a bracelet, in accordance with some embodiments.
Figure 4:
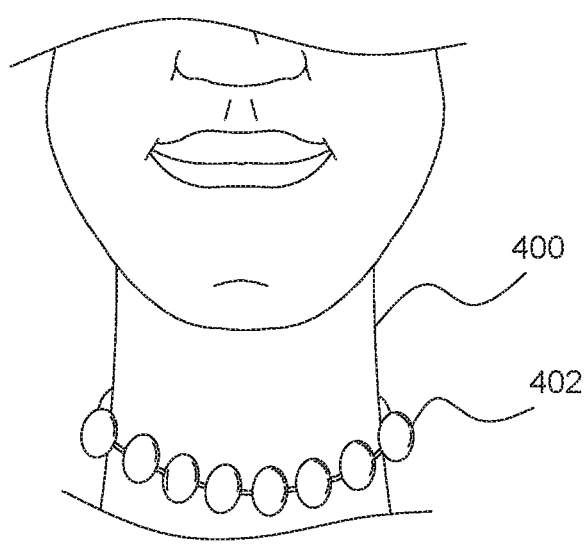
FIG. 4 shows an arrangement of capsule beads in the form of a necklace, in accordance with some embodiments.

FIG. 3 shows an arrangement of capsule beads in the form of a bracelet 304, in accordance with some embodiments. The bracelet 304 includes a plurality of capsule beads, each containing (initially) a topical material, arranged into a circle (i.e. without ends). The arrangement can be sized to fit around a person's wrist 302 and be retained against the person's hand 300. Similarly, FIG. 4 shows an arrangement of capsule beads in the form of a necklace 402, in accordance with some embodiments, that can be worn around a person's neck 400. Other arrangements of capsule beads can be realized as well, as will be appreciated by those skilled in the art. The plurality of beads need not be necessarily arranged in a circle, or sized to be carried on a person's body.

Figure 5:
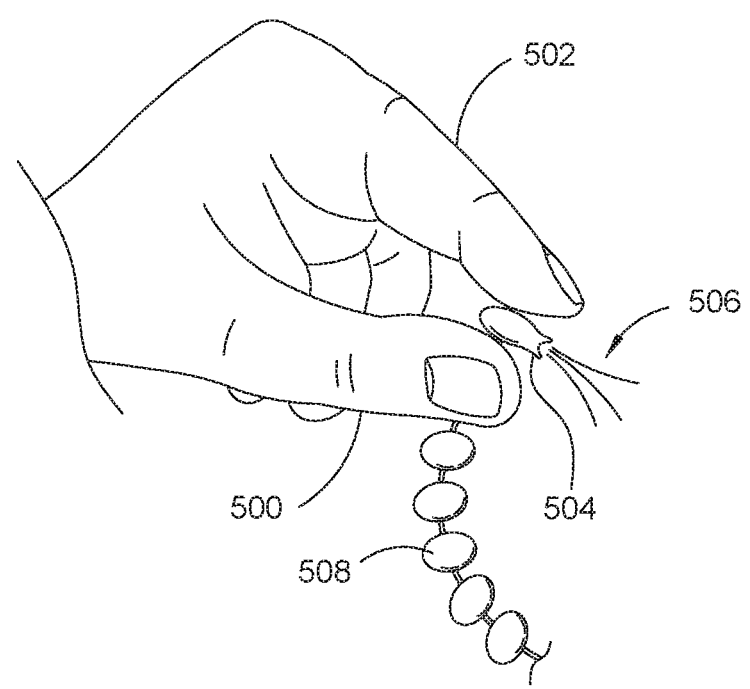
FIG. 5 shows a capsule bead being ruptured to dispense the topical material contained therein, in accordance with some embodiments.

FIG. 5 shows a capsule bead 504 being ruptured to dispense the topical material 506 contained therein, in accordance with some embodiments. The capsule bead 504 is shown being held between the tips of a person's thumb 500 and index finger 502 to apply pressure to the capsule bead, causing it to rupture or otherwise breach a portion of the capsule bead 504 to release the topical material 506. The pressure needed to rupture the capsule bead can be selected to prevent accidental ruptures, but should be low enough to allow the topical material 506 to be dispensed without it being under a pressure sufficient to cause it to spray undesirably from the capsule bead 504. In some embodiments the capsule beads can be configured to rupture under a pressure of about fifteen pounds per square inch. The emptied capsule bead 504 can remain coupled to the other capsule beads 508 for appropriate disposal.

Figure 6:
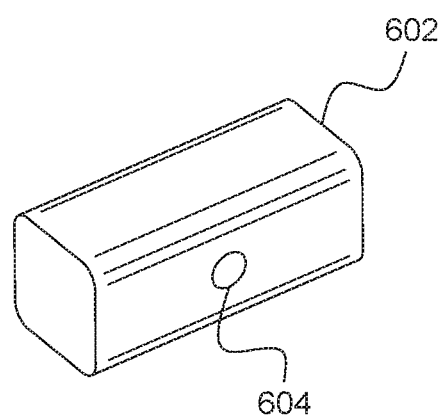
FIG. 6 shows an example of a capsule bead having a compliant hollow body and a rupturable port, in accordance with some embodiments.
Figure 8:
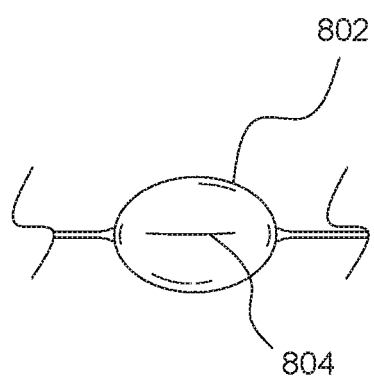
FIG. 8 shows a capsule bead having a score line to facilitate pressure-induced rupture, in accordance with some embodiments.

FIG. 6 shows an example of a capsule bead 600 having a compliant hollow body 602 and a rupturable port 604, in accordance with some embodiments. The body 602 is made of a compliant or compressible flexible material so that is can be squeezed and deformed under pressure. The body 602 shown here In order to allow a user to predict where the capsule bead will rupture, it is contemplated in some embodiments to include a port 604 in the form of a weakened portion or a portion that is otherwise configured to breach under a lower pressure than that which would be necessary to breach the body 602. Thus, when the body 602 is squeezed, the contents will be expelled from the port 604 once sufficient pressure to breach to port 604 is applied to the body 602. Similarly, FIG. 8 shows an ovoid capsule bead 802 that is scored 804 along a side of the capsule bead 802 to create a breach location which will rupture when a sufficient pressure is applied to the capsule bead 802, allowing a person to know where the contents of the capsule bead 802 will come out of the capsule bead 802.

Figure 7:
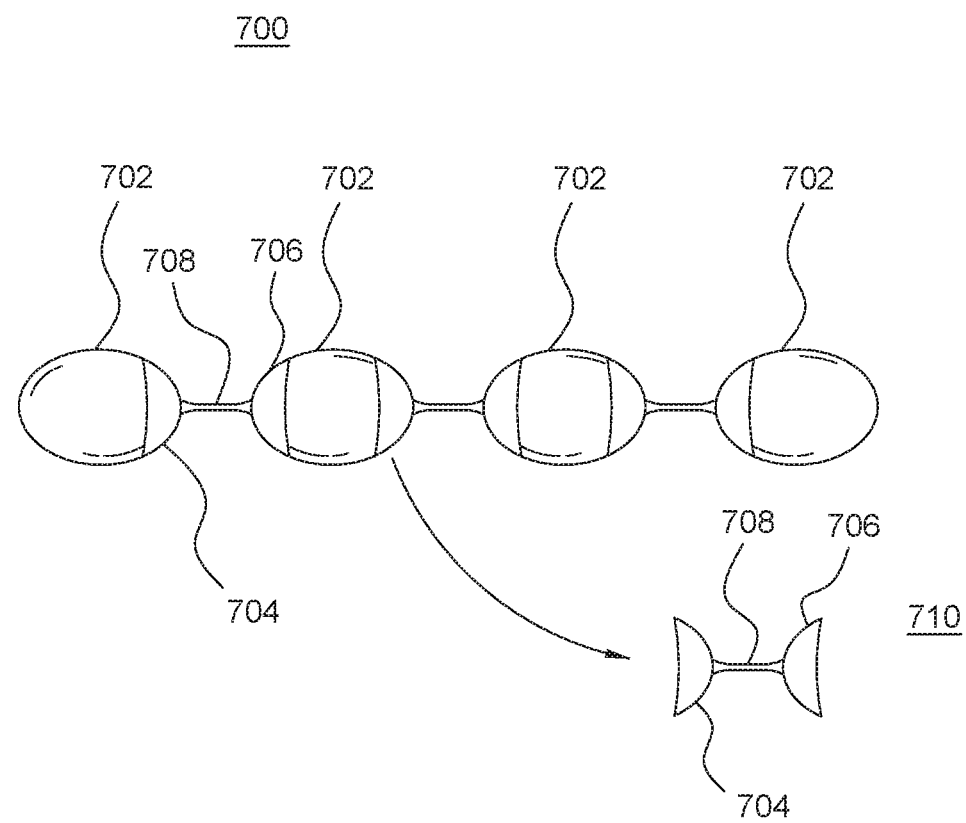
FIG. 7 shows a plurality of capsule beads coupled together by linkages, in accordance with some embodiments.

FIG. 7 shows a plurality of capsule beads 702 coupled together by linkages, in accordance with some embodiments, for an arrangement 700 of capsule beads. A particular type of linkage is exemplified here as a pair of oppositely facing coupling member 704, 704 which each couple to the end or side of a different capsule bead 702. The coupling members 704, 706 can be coupled to the respective capsule beads by an adhesive, or otherwise bonded to the material of the capsule bead. A flexible member 708 joins the coupling members together. The flexible member 708 can be integrally formed with the coupling members 704, 706, or it can be a separate member that is attached to the coupling member 704, 706. View 710 shows the linkage by itself, without being coupled the capsule beads 702.

Figure 9:
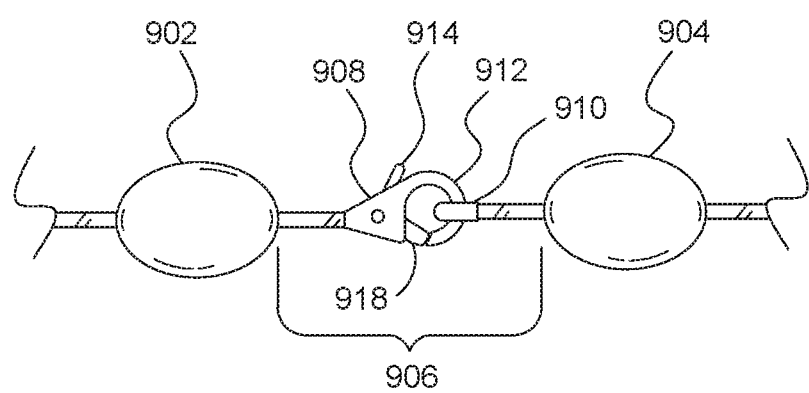
FIG. 9 shows a linkage or connecting member between capsule beads in the form of a clasp, in accordance with some embodiments.

FIG. 9 shows a linkage or connecting member between capsule beads in the form of a clasp, in accordance with some embodiments. A first capsule bead 902 and a second capsule beads 904 are opposite ends of a series of capsule beads and are joined together by linkage 906 in the form of a clasp. The clasp is comprises of a hook member 908 on one end, and a loop member 910 on the other end of the series of capsule beads. The loop member 910 has a loop or ring that goes over a hook 912 of the hook member 908, which is retained on the hook 912 by a gate 916 that is biased to a closed position by a spring, as is known. The gate 916 can be opened by pressing in a gate lever 914 to move the gate 916 into an open position which will allow the loop/ring to be removed from engagement with the hook 912. Other types of clasps are known and can be used equivalently. In general, a clasp joins the ends together in a way that holds them together but also allows a user to disjoin them so as to allow placement of the arrangement around a user's wrist, for example.

Figure 10:
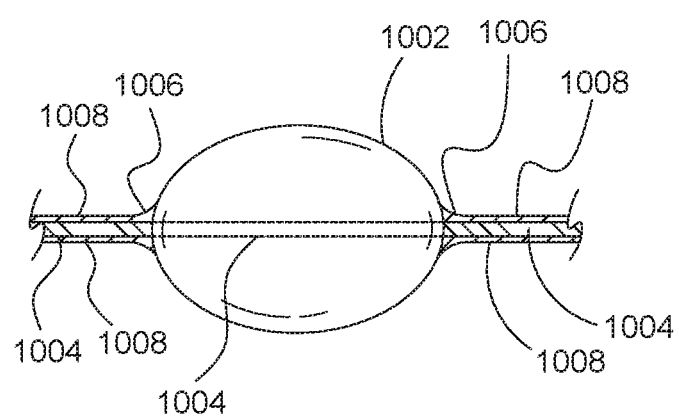
FIG. 10 shows a coated filament that passes through the capsule beads being used as a linkage or connecting member between capsule beads, in accordance with some embodiments.

FIG. 10 shows a filament 1004 that passes through the capsule beads being used as a linkage or connecting member between capsule beads, in accordance with some embodiments. The filament 1004 is shown passing through a capsule bead 1002 which is one capsule of a series of capsule beads, and the filament 1004 similarly passes through other capsule beads to join them together in the arrangement. The filament can be a thread, cord, string, or similarly flexible component. The capsule beads can be manufactured with the filament 1004 passing through them such that the ends 1006 of the capsule bead 1002 are sealed, and the filament 1004 is coated with a layer 1008 of the same material that forms the wall of the capsule bead 1002. In some embodiments the filament 1004 can be threaded through a filled capsule bead, and then sealed to prevent leakage such as by localized heating of the ends of the capsule bead 1002, or by a bonding agent placed on the filament 1004 at the location where it passes through the wall of the capsule bead 1002.

Figure 11:
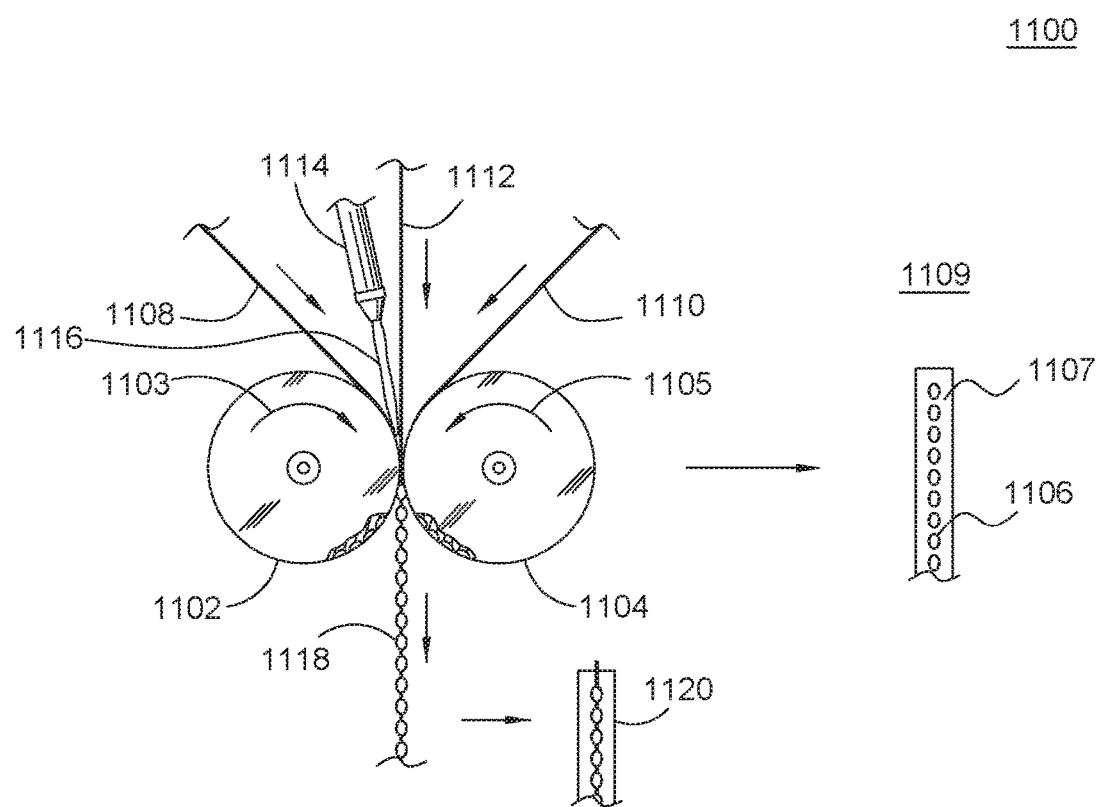
FIG. 11 shows a double die press machine for manufacturing capsule beads in accordance with some embodiments.

FIG. 11 shows a double die press machine 1100 for manufacturing capsule beads in accordance with some embodiments. A pair of rotating dies 1102, 1104 rotate in opposite directions as indicated by arrows 1103, 1105 and have a plurality of depressions 1106 in their opposing outside surfaces 1107 as seen in edge view 1109 of die 1104. The depressions 1106 of each die correspond as they rotate so that the depressions line up together in an opposing manner. Material is fed between the dies as they rotate to form a series of capsule beads that are linked together. The material includes a first feed 1108 of capsule bead wall material, and a second feed 1110 of capsule bead wall material. The feeds 1108, 1110 come from different directions and are heated to make the capsule bead wall material pliable. A filament 1112 is also fed between the feeds 1108, 1110. As the feeds 1108, 1110 and filament 1112 pass between the dies 1102, 1104, a pump 1114 pumps the topical material through a thin nozzle member 1116 between the feeds 1108, 1110 when there are depressions in the dies 1102, 1104 on either side of the material being fed, causing the heated material to displace outwards into the depressions 1106. At the same time, the surfaces 1107 of the dies 1102, 1104 are close enough to cause the material of the feeds 1108, 1110 to be pressed and bonded together, sealing the topical material and filament 1112 between the feeds of capsule bead wall material 1108, 1110. On the other side (below the dies) of the feed point, the bonded material 1118 emerges. In view 1120 the bonded material 1118 is seen as it would appear when turned ninety degrees, and the excesses bonded material can then be cut away to produce a series of capsule beads, linked together, that each contain a quantity of a topical material.

Figure 12:
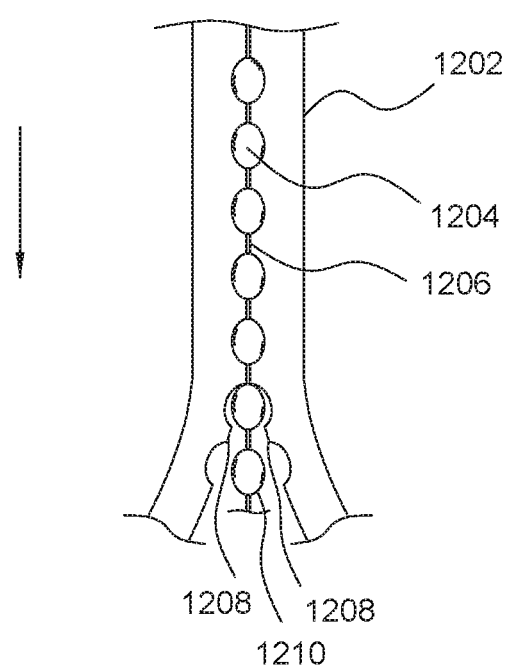
FIG. 12 shows separating process used in the manufacture of connected capsule beads, in accordance with some embodiments.

FIG. 12 shows a separating process 1200 used in the manufacture of connected capsule beads, in accordance with some embodiments. The process starts with the bonded material such as that shown in FIG. 11 (e.g. 1118 once cooled), and separates the excess material 1202 from the capsule beads 1204 and the linking filament 1206. A die or dies can be used to cut away the excess material 1202 to create edges 1208 on either side of the capsule beads and filament to produce freed capsule beads 1210. The die or dies used can be similar to dies 1102, 1104, with raised cutting features outside the depressions and between the depressions along the filament. Accordingly, the processes represented by FIGS. 11-12 can be used, in some embodiments, to manufacture a series of capsule beads filled with topical material. The series can be cut to produce segments of desired lengths to produce bracelets, necklaces or other arrangements, along with suitable means to joins the ends together.

A hand sanitizing apparatus has been disclosed that includes a series of rupturable capsule beads, that can contain a single use quantity of hand sanitizing fluid or gel. A user can rupture a capsule bead by squeezing it, where the pressure breaks a wall of the capsule bead, causing the fluid therein to be expelled (e.g. onto the user's hands). The disclosed apparatus therefore solves the problem of carrying hand sanitizer without having to carry a bottle of sanitizing material. The apparatus can be decorative, be formed in various colors (e.g. sports team colors), and so on. The capsule beads can also be filled with other types of material that a person may want to carry, such as moisturizing lotion.

What is claimed is:

1. A wearable hand sanitizing apparatus for dispensing a sanitizing fluid, comprising:
   a plurality of capsule beads, each of which is filled with a quantity of sanitizing fluid and having at least a portion that is configured to rupture upon a pressure being applied to the capsule bead, thereby allowing the sanitizing fluid to be dispensed from the capsule bead;
   a filament that passes through a wall of each one of the plurality of capsule beads at opposing ends of each capsule bead, wherein the capsule beads are sealed at each of the opposing ends where the filament passes through the capsule beads; and
   wherein the plurality of capsule beads are arranged on the filament to form a series of capsule beads connected by the filament.

2. The wearable hand sanitizing apparatus of claim 1, wherein at least some of the plurality of capsule beads each comprise a compressible hollow body and a rupturable port.

3. The wearable hand sanitizing apparatus of claim 1, wherein at least some of the plurality of capsule beads each comprise a hollow body having a spherical or ovoid shape.

4. The wearable hand sanitizing apparatus of claim 1, wherein the opposing sides of each one of the plurality of capsule beads is sealed by localized heating each of the opposing ends of each capsule bead.

5. The wearable hand sanitizing apparatus of claim 1, wherein one of the plurality of linkages comprises a clasp.

6. The wearable hand sanitizing apparatus of claim 1, wherein the opposing sides of each one of the plurality of capsule beads is sealed by a bonding agent placed on the filament at each opposing end of each capsule bead.

7. The wearable hand sanitizing apparatus of claim 1, wherein the filament is coated with a layer of material that is the same as, and contiguous with that used to form a wall of each one of the plurality of capsule beads, and which extends over the filament outside of the capsule beads at each opposing end of each capsule bead.

8. The wearable hand sanitizing apparatus of claim 1, wherein each of the plurality of capsule beads is made of a material including at least one of plastic, gelatin, cellulose, or silicone.

9. The wearable hand sanitizing apparatus of claim 1, wherein the plurality of capsule beads and linkages are arranged into a circle.

10. The wearable hand sanitizing apparatus of claim 9, wherein the circle is sized to fit on and be retained on a person's wrist.

11. The wearable hand sanitizing apparatus of claim 9, wherein the circle is sized to fit around a person's neck.

12. A bracelet for dispensing a hand sanitizing material, comprising:

a plurality of capsule beads, each of which is filled with a quantity of topical fluid and being configured to rupture upon a pressure being applied to the capsule bead, thereby allowing the topical fluid to be dispensed from the capsule bead; and a plurality of linkages, each linkage coupling two of the plurality of capsule beads together and wherein each one of the plurality of linkages is comprised of a pair of oppositely facing coupling members that are each configured to couple to an end of a different one of the plurality of capsule beads and wherein each pair of oppositely facing coupling members are joined together by a flexible member; and wherein the plurality of capsule beads and the plurality of linkages are arranged to form a series of capsule beads connected by the plurality of linkages.

13. The bracelet of claim 12, wherein at least some of the plurality of capsule beads each comprise a hollow body having a spherical or ovoid shape.

14. The bracelet of claim 12, wherein at least one of the plurality of capsule beads is visually distinct from the others of the plurality of capsule beads, and contains a topical fluid that is different from the topical fluid contained in the others of the plurality of capsule beads.

15. The bracelet of claim 12, wherein each of the plurality of capsule beads comprises a rupturable port.

16. The bracelet of claim 12, wherein each of the plurality of capsule beads is made of a material including at least one of plastic, gelatin, cellulose, or silicone.

\* \* \* \* \*